United States Patent
Hur et al.

(10) Patent No.: US 6,762,414 B2
(45) Date of Patent: Jul. 13, 2004

(54) APPARATUS FOR GENERATING ULTRAVIOLET RADIATION AND OZONE BY USING MICROWAVE

(75) Inventors: Bang-Uk Hur, Seoul (KR); Yoo-Byung Park, Seoul (KR)

(73) Assignee: Dae-won Paptin Foam Co. Ltd., Jeoneui-Myeon (KR)

(*) Notice: Subject to any disclaimer, the term of this patent is extended or adjusted under 35 U.S.C. 154(b) by 0 days.

(21) Appl. No.: 10/363,573

(22) PCT Filed: Sep. 18, 2001

(86) PCT No.: PCT/KR01/01558
§ 371 (c)(1),
(2), (4) Date: Feb. 28, 2003

(87) PCT Pub. No.: WO02/24236
PCT Pub. Date: Mar. 28, 2002

(65) Prior Publication Data
US 2004/0036034 A1 Feb. 26, 2004

(30) Foreign Application Priority Data
Sep. 19, 2000 (KR) .......................... 2000-55053

(51) Int. Cl.[7] ................................................ A61L 2/10
(52) U.S. Cl. .......................... 250/434; 250/435; 422/24
(58) Field of Search ................................ 250/434, 435; 422/24

(56) References Cited

U.S. PATENT DOCUMENTS 4,230,571 A * 10/1980 Dadd .......................... 210/760
2002/0098109 A1 * 7/2002 Nelson et al. ............... 210/748

* cited by examiner

Primary Examiner—John R. Lee
Assistant Examiner—James J. Leybourne
(74) Attorney, Agent, or Firm—Epstein Drangel Bazerman & James, LLP

(57) ABSTRACT

Disclosed is an apparatus for generating ultraviolet rays and ozone using microwaves to sterilize water in a swimming pool or potable liquids such as purified water, milk and juice and to eliminate impure organic matters contained in the water. The apparatus includes a housing (10) having an upper liquid inlet (12) and a lower liquid outlet (14), and defining a sterilization chamber (16) therein. The housing (10) includes therein a transparent partition wall (18), which is spaced from a side vertical wall of the housing (10) to serve as a side wall of the sterilization chamber (16). The transparent partition wall (18) is provided with several electrodeless ultraviolet lamps (20). Wave guides (22) are attached to the back faces of the electrodeless ultraviolet lamps (20), respectively, which are widened toward the ultraviolet lamps (20). Microwave generator units (24) are attached to back ends of the wave guides (22), respectively. The sterilization chamber (16) is provided at a bottom thereof with an air inlet pipe (26) and at a top thereof with an air outlet pipe (28).

1 Claim, 1 Drawing Sheet

APPARATUS FOR GENERATING ULTRAVIOLET RADIATION AND OZONE BY USING MICROWAVE

TECHNICAL FIELD

The present invention relates, in general, to an apparatus for generating ultraviolet rays and ozone using microwaves and, more particularly, to an apparatus for radiating ultraviolet rays and ozone generated by microwaves to potable liquids such as purified water, milk and juice to sterilize the potable liquids and to eliminate organic impurities contained in the potable liquids.

BACKGROUND ART

In general, potable liquids such as purified water, milk and juice, which is produced in large quantities to be supplied to consumers, are sterilized in various methods. Among the methods, a method for radiating ultraviolet rays or ozone to potable liquids to sterilize the liquids is well known. However, an apparatus for implementing the method is usually comprised of an ultraviolet radiator and an ozone radiator, both of which are manufactured separately from each other. Though there are combinations of the both radiators being used, ultraviolet lamps, which are employed in conventional ultraviolet radiators to generate ultraviolet rays, are operated by a voltage applied to electrodes, and are complicated in installations and structures thereof.

Moreover, though ozone radiators employ ultraviolet lamps, the ozone radiators have disadvantages in that it is impossible to efficiently penetrate ozone into objects to be treated. In particular, where it is required to sterilize a large amount of water as in swimming facilities, sterilization of water depends on only addition of chemicals because it is difficult to apply ultraviolet rays or ozone sterilization methods. Furthermore, since the chemicals used for sterilization are harmful to the human body, this sterilization method has been regarded as a serious problem.

DISCLOSURE OF THE INVENTION

Accordingly, the present invention has been made keeping in mind the above problems occurring in the prior art, and an object of the present invention is to provide an apparatus for generating ultraviolet rays and ozone using microwaves to sterilize potable liquids such as purified water, milk and juice to efficiently sterilize the potable liquids.

Another object of the present invention is to provide an apparatus for generating ultraviolet rays and ozone using electrodeless ultraviolet lamps, which are activated by microwaves.

A further object of the present invention is to provide an apparatus for generating ultraviolet rays and ozone using microwaves, which is adapted to sterilize and purify water in swimming facilities such as swimming pools as well as potable liquids.

In order to accomplish the above objects, the present invention provides an apparatus for generating ultraviolet rays and ozone using microwaves, which includes a housing having an upper liquid inlet and a lower liquid outlet and defines a sterilization chamber therein, comprising: a transparent partition wall disposed in the housing and defining the sterilization chamber; a plurality of electrodeless ultraviolet lamps mounted on the transparent partition wall such that the front faces of the electrodeless ultraviolet lamps face the sterilization chamber; a plurality of wave guides attached to the back faces of the electrodeless ultraviolet lamps, respectively, and widened toward the ultraviolet lamps; a plurality of microwave generator units attached to back ends of the wave guides; an air inlet pipe disposed at a bottom of the sterilization chamber and connected to a fine air bubble generator; and an air outlet pipe disposed at a top of the sterilization chamber.

BRIEF DESCRIPTION OF THE DRAWINGS

The above and other objects, features and other advantages of the present invention will be more clearly understood from the following detailed description taken in conjunction with the accompanying drawings, in which.

BEST MODE FOR CARRYING OUT THE INVENTION

Figure 1:
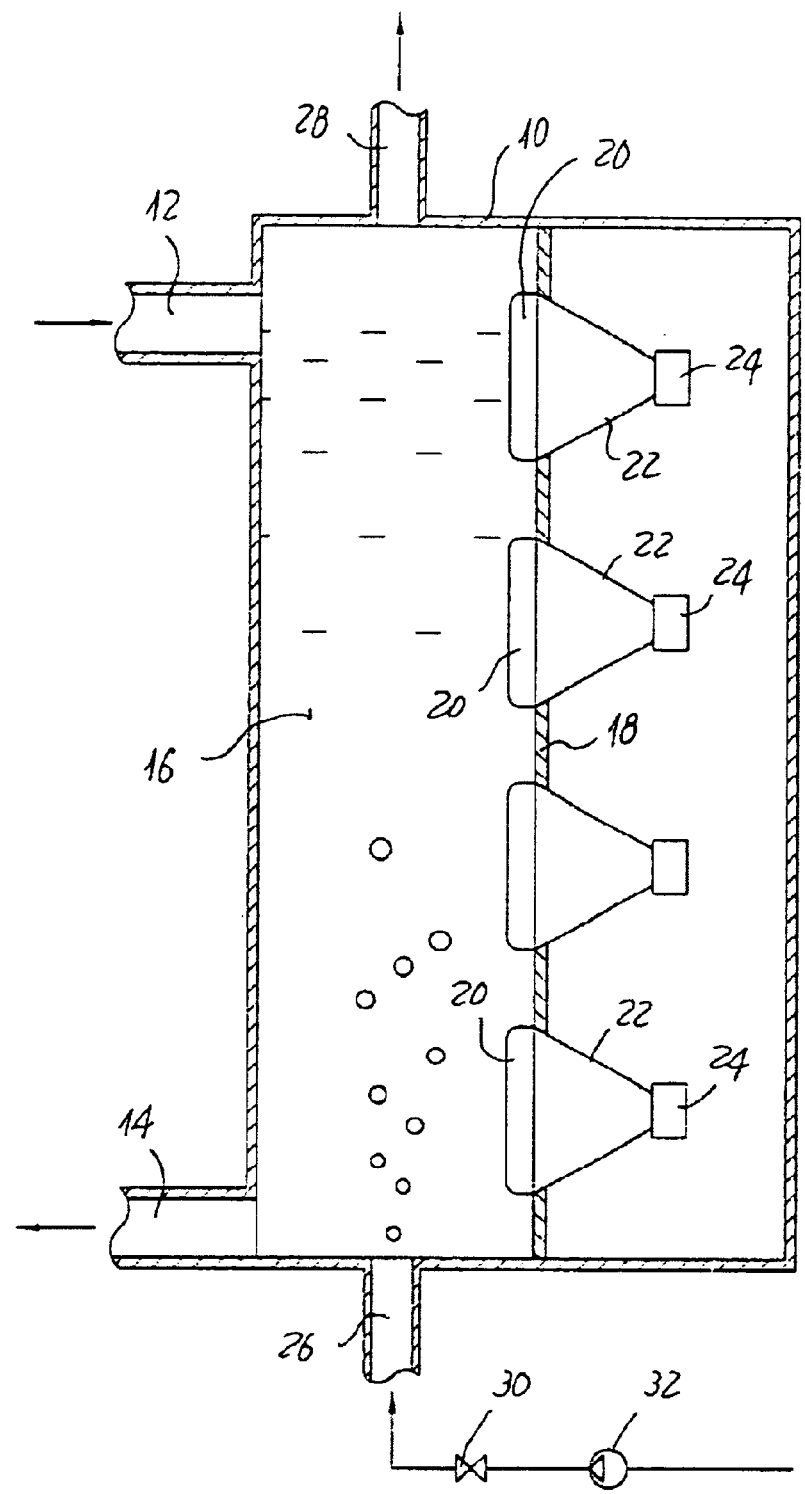
FIG. 1 is a cross-sectional view of an embodiment of the present invention.

Referring to FIG. 1, there is shown an apparatus for generating ultraviolet rays and ozone according to an embodiment of the present invention. The apparatus for generating ultraviolet rays and ozone according to the present invention includes a housing which is provided at its upper portion with a liquid inlet 12 and at its lower portion with a liquid outlet 14, and which defines a sterilization chamber 16 therein. The housing 10 is provided therein with a transparent partition wall 18, which is spaced from a side vertical wall of the housing 10 to serve as a side wall of the sterilization chamber 16, and through which ultraviolet rays can be transmitted. The transparent partition wall 18 is provided with several electrodeless ultraviolet lamps 20 in which argon and a bit of mercury (Hg) and helium (He) are filled such that the front faces of the electrodeless ultraviolet lamps 20 are disposed to face the sterilization chamber 16. Wave guides 22 are attached to the back faces of the electrodeless ultraviolet lamps 20, respectively, which are widened toward the ultraviolet lamps 20. The wave guides 22 are provided at back ends thereof with microwave generator units 24, respectively. The sterilization chamber 16 is provided at a bottom face of the housing 10 with an air inlet pipe 26 and at a top face of the housing 10 with an air outlet pipe 28 so that air introduced into the sterilization chamber through the air inlet 26 can flow back with respect to flow of the liquid such as potable liquids. The air inlet pipe 26 is connected to a typical fine bubble generator (not shown), so that air introduced into the sterilization chamber 16 is finely bubbled to be spread uniformly and rise. In the drawing, the reference number 30 which is not described indicates an air supply control valve, and the reference number 32 indicates an air supply pump.

In sterilization of potable liquids such as purified water, milk and juice using the apparatus according to the present invention, the liquid is introduced into the sterilization chamber 16 through the upper liquid inlet 12 of the housing 10 and then discharged through the lower liquid outlet 14 while air is introduced into the sterilization chamber 16 through the lower air inlet 26 and then discharged through the upper air inlet 28 so that the air introduced into the sterilization chamber 16 flows against the flow of the potable liquid. While the counterflows of the potable liquid and the air continue, microwaves are generated from the typical microwave generator units 24. The microwaves generated from the microwave generator units 24 act on the electrodeless ultraviolet lamps 20 through the wave guides 22, so that the gas such as argon filled in the ultraviolet lamps 20 is excited, thereby causing ultraviolet rays to be generated. The ultraviolet rays radiated from the ultraviolet lamps 20 are projected to the potable liquid downwardly flowing in the sterilization chamber 16 to sterilize the potable liquid, and at the same time act on fine air bubbles dispersed in the potable liquid and upwardly flowing against the flow of the potable liquid to cause oxygen in the air to be partially oxidized to ozone, thereby allowing the ozone to kill bacteria contained in the potable liquid and to destroy harmful organic matters included in the water.

When the apparatus according to the present invention is applied to sterilization procedure for water in a swimming facility such as a swimming pool, the apparatus for generating ultraviolet rays and ozone using microwaves is installed at an appropriate position in the swimming pool, and water in the swimming pool is introduced thereinto through the liquid inlet 12 by a pump (not shown). Thereafter, the introduced water is sterilized in the same way as the above-described sterilization of potable liquid, and then discharged to the swimming pool through the liquid outlet 14. With such continuous circulation of the water through the apparatus, the water in the swimming pool can be completely sterilized and purified.

Industrial Applicability

According to the present invention, since ultraviolet rays and ozone are concurrently produced from the apparatus of the present invention, sterilization of potable liquids such as purified water, milk and juice, which are produced in large quantities and supplied to consumers, can be more reliably fulfilled. Furthermore, the apparatus according to the present invention is capable of sterilizing a large amount of water in a swimming pool by ultraviolet rays and ozone, rather than chemicals harmful to a human body.

What is claimed is:

1. An apparatus for generating ultraviolet rays and ozone using microwaves, which includes a housing having an upper liquid inlet and a lower liquid outlet and defines a sterilization chamber therein, comprising:

a transparent partition wall disposed in the housing and defining the sterilization chamber;

a plurality of electrodeless ultraviolet lamps mounted on the transparent partition wall such that the front faces of the electrodeless ultraviolet lamps face the sterilization chamber;

a plurality of wave guides attached to the back faces of the electrodeless ultraviolet lamps, respectively, and widened toward the ultraviolet lamps;

a plurality of microwave generator units attached to back ends of the wave guides;

an air inlet pipe disposed at a bottom of the sterilization chamber and connected to a fine air bubble generator; and an air outlet pipe disposed at a top of the sterilization chamber.

* * * * *